United States Patent
Pineau et al.

(10) Patent No.: US 6,242,229 B1
(45) Date of Patent: *Jun. 5, 2001

(54) COSMETIC/PHARMACEUTICAL COMPOSITIONS COMPRISING MICROORGANISM CULTURE MEDIA

(75) Inventors: Nathalie Pineau, Poitiers; Richard Martin, Rochecorbon; Lionel Breton, Versailles; Lucien Aubert, Cap D'Ail, all of (FR)

(73) Assignee: Societe L'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/072,560

(22) Filed: May 5, 1998

(30) Foreign Application Priority Data

May 5, 1997 (FR) .................................................. 97 05510

(51) Int. Cl.⁷ .................................................... A61K 35/66
(52) U.S. Cl. ............................................ 435/170; 435/261
(58) Field of Search ................................ 424/195.1, 93.4; 435/170, 261

(56) References Cited

U.S. PATENT DOCUMENTS

| 5,618,521 | * | 4/1997 | de Rigal et al. ........................ 424/59 |
| 5,780,424 | * | 7/1998 | Pineau et al. ............................. 514/2 |
| 5,795,574 | * | 8/1998 | Breton et al. ....................... 424/195.1 |
| 6,190,672 | * | 2/2001 | Aubert et al. ....................... 424/282.1 |

FOREIGN PATENT DOCUMENTS

| 0761204 | 3/1997 | (EP) . |
| 0765667 | 4/1997 | (EP) . |
| 2034687 | 6/1980 | (GB) . |
| WO94/02158 | 2/1994 | (WO) . |

* cited by examiner

*Primary Examiner*—Jean C. Witz
(74) *Attorney, Agent, or Firm*—Burns, Doane, Swecker & Mathis, L.L.P.

(57) ABSTRACT

Cosmetic/pharmaceutical compositions, suitable for cosmetic applications and/or for treating a wide variety of mammalian disorders or disease states, comprise an effective active principle amount of a clarified and stabilized culture medium for at least one non-photosynthetic filamentous bacterium, advantageously belonging to the genera Beggiatoa, Vitreoscilla, Flexithrix or Leucothrix, formulated into a cosmetically/pharmaceutically acceptable vehicle, diluent or carrier therefor.

16 Claims, No Drawings

COSMETIC/PHARMACEUTICAL COMPOSITIONS COMPRISING MICROORGANISM CULTURE MEDIA

CROSS-REFERENCE TO PRIORITY APPLICATION

This application claims priority under 35 U.S.C. §119 of FR-97/05510, filed May 5, 1997, hereby expressly incorporated by reference.

BACKGROUND OF THE INVENTION

1. Technical Field of the Invention

The present invention relates to cosmeticlpharmnaceutical compositions comprising, as an active principle therein, an effective amount of culture medium for at least one non-photosynthetic filamentous bacterium, said medium being clarified and stabilized.

The present invention also relates to cosmetic treatments comprising administration of the aforesaid compositions.

2. Description of the Prior Art

It is known to this art to employ microorganisms in cosmetics or in pharmacy, principally in the form of extracts, for their art-recognized properties.

By the term "extract" is intended a product corresponding to a microorganism biomass which, after culturing and once separated from its culture medium, is subjected to various treatments which can range from simple freezing of the biomass to very elaborate purifications of microorganism constituents.

Exemplary are yeast extracts used in cosmetics, bacteria used for the preparation of milk products, bacterial extracts used as bactericides, as cicatrizing agents or, alternatively, as immunostimulants.

More particularly representative is the formulation, into cosmetics, of ribosomal fractions, for example in the preparation of compositions intended to retard aging of the skin by stimulating cell growth and modifying the maturation of connective tissue (EP-A-631,773).

In medicine, compositions for reinforcing the immune defenses are known, in particular for patients who have suffered serious burns and are consequently sensitive to the opportunist infections caused by bacteria, viruses or fungi (WO-91/11174) or, alternatively, as regards diseases of the otorhinolaryngology sphere (FR-2,253,499, FR-2,360,314, FR-2,388,563, FR-2,674,755 and ZA-8801071) or allergies (U.S. Pat. No. 4,946,945).

These compositions generally comprise preparations of microorganism ribosomal fractions.

This is a class of bacteria for which many properties have been demonstrated and which are useful both in cosmetics and in pharmacy. They are the class of filamentous, non-photosynthetic bacteria as defined according to the classification in Bergey's *Manual of Systematic Bacteriology* (Vol. 3, Sections 22 and 23, 9th edition, 1989).

These bacteria, several of which have already been described, generally exist in an aquatic habitat and can be found, in particular, in marine waters or in thermal springs.

These bacteria, or extracts thereof, are described in FR-2,283,223 for their anti-inflammatory and cicatrizing properties, their antiacne and antiseborrhoeic power and their ability to promote moisturization of the skin.

EP-A-0,681,831 describes the formulation of these bacteria or of extracts thereof into cosmetic compositions intended to combat aging of the skin.

The reason for this is that such bacteria or extracts thereof exhibit properties in the field of epidermal renewal.

EP-A-0,761,204 describes these bacteria or extracts thereof for the soothing of sensitive skin, this property moreover being attributed to their substance P-antagonist property.

In WO-94/02158 and in EP-A-0,765,667 the immunostimulatory properties of these bacteria or extracts thereof are described for applications in cosmetics and in pharmacy.

In all of these applications, the active agent is the bacterial biomass, separated from its culture medium and optionally having been subjected to various treatments.

The production of this biomass requires specific growth conditions which make it delicate and increases the time required for the preparation, as well as the cost of this starting material.

SUMMARY OF THE INVENTION

It has now surprisingly and unexpectedly been determined that the culture medium of non-photosynthetic filamentous bacteria, which has been clarified and stabilized, to date considered as being of no value at the end of the culturing and removed, indeed exhibits properties similar to those of the biomass.

Furthermore, even more unexpectedly, the level of expression of these properties by the medium is completely comparable to that of the biomass.

The advantage presented by such phenomenon is immediately apparent, in particular because it is known that culturing, in a 300 liter fermenter, only produces between 270 grams and 360 grams maximum dry weight of biomass.

Thus, the present invention features cosmetic/pharmaceutical compositions comprising, in a cosmetically and/or pharmaceutically acceptable vehicle, diluent or carrier, an effective amount of a culture medium for at least one non-photosynthetic filamentous bacterium, said medium being clarified and stabilized.

DETAILED DESCRIPTION OF BEST MODE AND SPECIFIC/PREFERRED EMBODIMENTS OF THE INVENTION

More particularly according to the present invention, by the expression "cosmetically and/or pharmaceutically acceptable vehicle, diluent or carrier" is intended any physiologically acceptable support substrate.

By the expression "clarified culture medium" is intended a culture medium which has been employed to amplify a microorganism, in particular a bacterium, which, after amplification of said microorganism, has been subjected to a manipulation entailing physically separating it from said culture medium and from said microorganism.

By the expression "stabilized culture medium" is intended a culture medium which has been subjected to a manipulation for preserving it in the state in which it was found at a selected given instant, while at the same time conserving its intrinsic properties. In particular, when this is a microorganism culture medium, this manipulation is intended, for example, to render the medium sterile, i.e., incapable of permitting the growth of microorganisms while at the same time preserving, for example, any biological properties it may have.

Exemplary non-photosynthetic filamentous bacteria according to the invention are preferably those of the order of Beggiatoales. Even more particularly preferred bacteria are those of the genera Beggiatoa, Vitreoscilla, Flexithrix or Leucothrix.

Exemplary such bacteria include:

*Vitreoscilla filiformis* (ATCC 15551)
*Vitreoscilla beggiatoides* (ATCC 43181)
*Beggiatoa alba* (ATCC 33555)
*Flexithrix dorotheae* (ATCC 23163)
*Leucothrix mucor* (ATCC 25107)
*Sphaerotilus natans* (ATCC 13338)

A strain of *Vitreoscilla filiformis* is preferably employed according to the invention.

In order to prepare useful culture media according to the invention, the bacteria can be cultured according to techniques well known to this art. In this regard, all details required for culturing these bacteria are set forth in Bergey's *Manual of Systematic Bacteriology* (9th edition, 1989).

It is known to the art that non-photosynthetic filamentous bacteria are relatively difficult to culture, and the production of pure cultures is likewise difficult. Most researchers recommend the use of poorly defined media, including various macerations using tap water. The carbon source recommended is an acetate.

Preferably, the culture medium according to the invention is the culture medium which allowed the preparation of a biomass of non-photosynthetic filamentous bacteria per the process described in WO-94/02158, assigned to the assignee hereof.

It has thus been shown that it is possible to adapt these bacteria, by counter-selection, to the use of an ose, instead of acetate, as a carbon source.

It has also been shown that it is possible to culture these bacteria on a fully defined culture medium. Culturing can be carried out, in particular, in the following medium:

| COMPOSITION | CONCENTRATION |
|---|---|
| Autolytic yeast extract | 0.5 to 5 g/l |
| Peptone | 0.5 to 5 g/l |
| Anhydrous glucose | 0.5 to 7 g/l |
| Heller microelements | 0.5 to 5 ml/ |
| CaCl$_2$.10H$_2$O | 0.01 to 0.20 g/l |

The mixture is diluted to 1000 ml with distilled water. Exemplary peptones include soybean papain peptone.

This specific medium differs from the media generally employed by the absence of catalase and of sulfide, although these ingredients were generally hitherto considered as essential.

The Heller microelements, the composition of which is set forth below, were described by Heller, *Ann Sci. Nat. Biol. Veg.*, 14, 1–223 (1953).

These are mixtures of various inorganic elements which have been recommended by Heller, not for culturing bacteria but for nourishing plant tissues grown in vitro. It should be noted here that it was not sought to determine whether the Heller microelements are all essential or useful for culturing nonphotosynthetic filamentous bacteria. However, it was determined that the Heller microelements used together, in combination with the other constituents indicated in the above table, effectively permit the bacteria under consideration to be cultured.

The composition of the Heller microelements, per 1 liter of distilled water, is as follows:

| | |
|---|---|
| ZnSO$_4$.7H$_2$O | 1 g |
| MnSO$_4$.H$_2$O | 0.076 g |
| CuSO$_4$.5H$_2$O | 0.003 g |
| KI | 0.010 g |
| H$_3$BO$_3$ | 1 g |
| AlCl$_3$.6H$_2$O | 0.050 g |
| NiCl$_2$.6H$_2$O | 0.030 g |

The culturing can be carried out at an appropriate temperature which is suitable for the bacterial species cultured. Generally, this temperature is between 18° and 40° C. depending on the strains. The pH of the culture medium is preferably between 5.5 and 8.

When the bacterial culture has reached a terminal stage, namely, in general, when the biomass is at the end of exponential growth, the biomass is separated from the culture medium. This separation can be effected by any standard technique such as, for example, centrifugation, filtration, coagulation with an alcohol (ethanol, isopropanol, isobutanol) or drying on a scraped cylinder with a prelayer (starch, diatoms, etc.).

Centrifugation is the preferred method.

In this case, the culture medium can be stabilized by any known technique. By way of example, suitable is sterilizing filtration, autoclaving, ultra-high temperature (UHT technique), high-pressure sterilization, γ-radiation or freezing.

Preferably, stabilization by autoclaving is carried out. Advantageously, the autoclaving is carried out at a temperature between 115° C. and 121° C. and preferably for a period of time from 15 to 40 minutes.

One example of the preparation of a culture medium according to the invention is set forth in the examples below.

The amount of clarified and stabilized culture medium for at least one non-photosynthetic filamentous bacterium, for formulation into the compositions of the invention, depends, of course, on the desired effect. It can thus vary over very wide limits.

In order to provide an order of magnitude, the composition can contain an amount of a culture medium for at least one non-photosynthetic filamentous bacterium constituting from 0.0001% to 30% of the total weight of the composition and preferably an amount constituting from 0.01% to 15% of the total weight of the composition.

The subject compositions can be ingested, injected or topically applied to the skin (to any area of body skin), the hair, the nails or mucous membranes (buccal, jugal, gingival, genital or connective). According to the mode of administration, the composition according to the invention can be in any conventional pharmaceutical form.

For topical application to the skin, the composition can be in the form, especially, of an aqueous or oily solution or a dispersion of the lotion or serum type, emulsions of liquid or semi-liquid consistency of the milk type, obtained by dispersing a fatty phase in an aqueous phase (O/W) or, conversely, (W/O), or of suspensions or emulsions of soft consistency of the aqueous or anhydrous gel or cream type, or alternatively microcapsules or microparticles, or vesicle dispersions of ionic and/or nonionic type. These compositions are formulated according to the usual techniques.

They can also be used for the hair in the form of aqueous, alcoholic or aqueous-alcoholic solutions, or in the form of creams, gels, emulsions or foams or, alternatively, in the form of aerosol compositions also comprising a propellent under pressure.

For injection, the subject compositions can be formulated as an aqueous or oily lotion or in the form of a serum. For the eyes, they can be in the form of drops, and for ingestion, they can be in the form of wafer capsules, granules, syrups or tablets.

The amounts of the various constituents of the compositions according to the invention are those conventionally employed in the fields considered.

These compositions especially constitute cleansing, protective, treatment or care creams for the face, for the hands, for the feet, for the major anatomical folds or for the body (for example day creams, night creams, makeupremoving creams, foundation creams or sunscreen creams), fluid foundations, makeup-removing milks, protective body milks, bodycare milks, sunscreen milks, skincare lotions, gels or mousses, for example cleansing lotions, sunscreen lotions, artificial tanning lotions, bath compositions, deodorizing compositions comprising a bactericidal agent, aftershave gels or lotions, hair-removing creams, insect repellants, pain-relief compositions, compositions for treating certain skin diseases such as eczema, acne rosacea, psoriasis, lichens and severe pruritus.

The compositions according to the invention can also comprise solid preparations constituting cleansing soaps or bars.

The compositions can also be packaged in the form of an aerosol composition also comprising a propellant under pressure.

The compositions according to the invention can also comprise a haircare composition, and especially a shampoo, a hairsetting lotion, a treating lotion, a styling gel or cream, a dye composition (in particular an oxidation dye composition) optionally in the form of dye-shampoos, restructuring lotions for the hair, a permanent-waving composition (in particular a composition for the first stage of a permanent-waving operation), a lotion or gel for preventing hair loss, an antiparasitic shampoo, etc.

The subject compositions can also be formulated for buccodental use, for example as a toothpaste. In this event, the composition can contain adjuvants and additives that are common in compositions for buccal use and, in particular, surfactants, thickeners, wetting agents, polishing agents such as silica, various active ingredients such as fluorides, in particular sodium fluoride, and optionally sweeteners such as sodium saccharinate.

When the composition is formulated as an emulsion, the proportion of the fatty phase can range from 5% to 80% by weight, and preferably from 5% to 50% by weight, relative to the total weight of the composition. The oils, the waxes, the emulsifiers and the co-emulsifiers formulated into the composition in emulsion form are selected from among those that are conventional in the cosmetic art. The emulsifier and the co-emulsifier are advantageously present in the subject compositions in a proportion ranging from 0.3% to 30% by weight, and preferably from 0.5 to 20% by weight, relative to the total weight of the composition. The emulsion can also contain lipid vesicles.

When the composition is an oily gel or solution, the fatty phase can constitute more than 90% of the total weight of the composition.

In known manner, the cosmetic compositions can also contain additives and adjuvants that are common in the cosmetic field, such as hydrophilic or lipophilic gelling agents, hydrophilic or lipophilic additives, preservatives, antioxidants, solvents, fragrances, fillers, sunscreens, odor absorbers and dyestuffs and colorants. The amounts of these various additives and adjuvants are those conventional in the cosmetic field, and, for example, range from 0.0 1% to 10% of the total weight of the composition. Depending on their nature, these additives and adjuvants can be introduced into the fatty phase, into the aqueous phase and/or into the lipid spherules.

Exemplary oils and waxes according to the invention include mineral oils (liquid petroleum jelly), plant oils (liquid fraction of carite butter, sunflower oil), animal oils (perhydrosqualene), synthetic oils (purcellin oil), silicone oils or waxes (cyclomethicone) and fluoro oils (perfluoropolyethers), beeswax, carnauba wax or paraffin wax. Fatty alcohols and fatty acids (stearic acid) can be added to these oils.

Exemplary emulsifiers include glyceryl stearate, polysorbate 60 and the mixture PEG-6/PEG-32/glycol stearate, marketed under the trademark Tefose$^R$63 by Gattefosse.

Exemplary solvents include the lower alcohols, in particular ethanol and isopropanol, and propylene glycol.

And exemplary hydrophilic gelling agents include the carboxyvinyl polymers (carbomer), acrylic copolymers such as acrylate/alkylacrylate copolymers, polyacrylamides, polysaccharides such as hydroxypropylcellulose, natural gums and clays, and, as lipophilic gelling agents, include the modified clays such as bentones, metal salts of fatty acids such as aluminum stearates and hydrophobic silica, ethylcellulose and polyethylene.

The subject compositions can contain other hydrophilic active agents such as proteins or protein hydrolysates, amino acids, polyols, urea, allantoin, sugars and sugar derivatives, water-soluble vitamins, plant extracts and hydroxy acids.

Retinol (vitamin A) and derivatives thereof, tocopherol (vitamin E) and derivatives thereof, essential fatty acids, ceramides, essential oils, and salicylic acid and derivatives thereof are representative lipophilic active agents.

According to the invention, the subject compositions can comprise other active agents intended, in particular, for the prevention and/or treatment of skin afflictions. Exemplary such active agents include:

(a) agents which decrease skin differentiation and/or proliferation and/or pigmentation, such as retinoic acid and its isomers, retinol and its esters, vitamin D and its derivatives, oestrogens such as oestradiol, kojic acid or hydroquinone;

(b) antibacterial agents such as clindamycin phosphate, erythromycin or antibiotics of the tetracycline class;

(c) antiparasitic agents, in particular metronidazole, crotamiton or pyrethroids;

(d) antifungal agents, in particular compounds of the imidazole class such as econazole, ketoconazole or miconazole or their salts, polyene compounds such as amphotericin B, compounds of the allylamine family such as terbinafine, or alternatively octopirox;

(e) antiviral agents such as acyclovir;

(f) steroidal anti-inflammatory agents such as hydrocortisone, betamethasone valerate or clobetasol propionate, or non-steroidal anti-inflammatory agents such as ibuprofen and its salts, diclofenac and its salts, acetylsalicylic acid, acetaminophen or glycyrrhetinic acid;

(g) anaesthetics such as lidocaine hydrochloride and its derivatives;

(h) antipruriginous agents such as thenaldine, trimeprazine or cyproheptadine;

(i) keratolytic agents such as α- and β-hydroxycarboxylic acids or β-ketocarboxylic acids, their salts, amides or esters and more particularly hydroxy acids such as glycolic acid, lactic acid, salicylic acid, citric acid and fruit acids in general, and 5-n-octanoylsalicylic acid;

(j) anti-free-radical agents such as a-tocopherol or its esters, superoxide dismutases, certain metal-chelating agents or ascorbic acid and its esters;

(k) antiseborrhoeic agents such as progesterone;

(l) antidandruff agents such as octopirox or zinc pyrithione;

(m) antiacne agents such as retinoic acid or benzoyl peroxide.

Thus, the compositions according to the invention can also comprise at least one active agent selected from among antibacterial agents, antiparasitic agents, antifungal agents, antiviral agents, anti-inflammatory agents, antipruriginous agents, anaesthetics, keratolytic agents, anti-free-radical agents, antiseborrhoeic agents, antidandruff agents, antiacne agents and/or agents which modify skin differentiation and/or cellular proliferation and/or pigmentation.

It is known to this art that aging of the skin, whether due to age or to other factors such as environmental factors, is reflected, in particular, by a deterioration of the mechanical properties of the skin, and in particular a loss of elasticity and of tonicity with the appearance of wrinkles. This phenomenon is associated in particular with adverse changes in the elastic tissues and especially a decrease in the number and diameter of the elastic fibers. Aging of the skin is also accompanied by a thinning of all of the skin components, the consequence of this being an increase in the fragility of the skin. Rarefaction of the fibroblasts along with an adverse change in their activity are considered as playing a very important role in the process of aging of the skin. It is also known that gas exchanges occur at the surface of the skin, with removal of carbon dioxide and absorption of oxygen. This phenomenon, deemed skin respiration, decreases with age and this decrease is considered as being a result of the decrease in epidermal activity.

It has now been found that the clarified and stabilized culture medium for at least one non-photosynthetic filamentous bacterium is capable of reducing and/or delaying aging of the skin, when topically applied thereto.

In particular, it has now been found that the culture medium is capable of modifying the gas exchanges across the skin, of stimulating the proliferation of fibroblasts and thus of improving the mechanical properties of the epidermis.

Thus, the invention also features a cosmetic treatment intended to reduce and/or delay aging of the skin, such that a cosmetic composition as described above is topically applied to the skin, to the scalp and/or to mucous membranes.

This invention also features pharmaceutical compositions intended to reduce and/or delay aging of the skin, comprising an effective amount of a culture medium for at least one non-photosynthetic filamentous bacterium as described above.

The immune system comprises a set of specialized cells which are subjected to a plurality of control mechanisms which ensure their renewal, their activation and their differentiation, these being essential for a normal level of immunocompetence. The role of the immune system is to discriminate the self from the non-self in order to eliminate pathogens and spontaneous tumors. Any cellular depletion, any immune-system dysregulation or any functional deficiency is apt to promote the occurrence of pathological manifestations characterized by disruption of the mechanisms for recognizing the self as opposed to the non-self, and a greater sensitivity with respect to microbial attack and neoplastic processes.

The skin constitutes the largest organ in the body and is recognized as one of the principal active elements of the immune defense system. Three types of epidermal cells participate in this system: keratinocytes, melanocytes and Langerhans cells. These cells, which are found only in the skin, play a fundamental role in the immune response and in particular in antigen presentation.

Healthy skin is capable of defending itself against external attack by virtue of the means at its disposal. However, it is subject to continual attack from the environment, chemical species and radiations. In particular, the Langerhans cells are the preferred target for ultraviolet radiation.

These lines of attack are reflected by an effect of suppression of the immune defenses, resulting in a lowering of the resistance to pathogens and an increase in the incidence of certain cancers.

In order to assist the skin in carrying out its immune function, products for stimulating the skin immune system are of great value.

It is known, moreover, that the immune system, and more particularly that of the skin, becomes impaired over the course of chronobiological aging.

This impairment also occurs over the course of photoinduced aging.

In this case, an inmunostimulatory effect can reestablish the immune functions, and more particularly those of the epidermis, by strengthening the natural defenses of the skin.

It thus has been found that the application of an effective amount of clarified and stabilized culture medium for at least one non-photosynthetic filamentous bacterium makes it possible to stimulate the immune system, more particularly the immune system of the skin.

In particular, the medium or the composition is intended to stimulate the immune defenses over the course of chronobiological aging, as well as over the course of light-induced aging.

This invention, hence, also features a cosmetic treatment intended to stimulate the immune defenses, such that a cosmetic composition as described above is topically applied to the skin, to the hair and/or to mucous membranes. Especially, this cosmetic treatment is intended to stimulate the immune defenses over the course of chronobiological aging, as well as over the course of light-induced aging.

Too, this invention features pharmaceutical compositions intended to stimulate the immune system, comprising an effective amount of a culture medium for at least one non-photosynthetic filamentous bacterium, as described above.

Polypeptides belonging to the tachykinin family exist in mammals, these polypeptides inducing rapid contractions on smooth muscle fibers. Exemplary compounds of this family include β-neurokinin, α-neurokinin and substance P.

Substance P is a polypeptide (undecapeptide) produced and released by a nerve ending. The localization of substance P is specific for neurons, both in the central nervous system and in the peripheral organs. Thus, a great many organs or tissues receive afferences of neurons with substance P; these are, in particular, the salivary glands, the stomach, the pancreas, the intestine (in the intestine, the distribution of substance P is superposed on the Meissner and Auerbach intrinsic nerve plexus), the cardiovascular system, the thyroid gland, the skin, the iris and ciliary bodies, the bladder and, of course, the central and peripheral nervous system.

Taking account of the ubiquitous distribution of substance P, a great many disorders are associated with a synthetic excess and/or release of substance P.

Substance P is involved, in particular, in pain transmission and in disorders of the central nervous system (for example anxiety, psychosis, neuropathy, neurodegenerative disorders such as Alzheimer's senile dementia, AIDS-related dementia, Parkinson's disease, Down's syndrome, Korsakoff's syndrome, multiple sclerosis, schizophrenia), in respiratory diseases (for example bronchopneumonias) and inflammatory diseases (for example rheumatoid polyarthritis), in allergic syndromes (for example asthma, allergic rhinitis, allergic pharyngitis, urticaria, eczematous dermatitis), in gastrointestinal diseases (for example ulcers, colitis, Crohn's disease), in skin disorders (for example psoriasis, pruriginous diseases, herpes, photodermatosis, atopic dermatitis, contact dermatitis, lichens, prurigo, pruritus, insect bites), in fibrosis and other disorders of collagen maturation (for example sclerodermia), in cardiovascular disorders, in vasospastic disorders (for example migraines, Reynaud's disease), in immunological disorders, in disorders of the urinary tract (for example incontinence, cystitis), in rheumatic diseases, in certain dermatological diseases (such as eczema) and in ophthalmological complaints (for example conjunctivitis, uveitis, ocular pruritus, pain in the eyes and irritations).

The use of a substance P antagonist is one of the effective therapeutic alternatives in all of the conditions and afflictions indicated above.

By the term "substance P antagonist" is intended any compound or active species capable of partially, or even totally, inhibiting the biological effects of substance P.

For a substance to be recognized as a substance P antagonist, it must induce a coherent pharmacological response (which may or may not include its binding to the substance P receptor), in particular in one of the following tests:

(1) the antagonist substance must reduce the extravasation of plasma across the vascular wall induced by capsaicin or by antidromic nerve stimulation, or alternatively, (2) the antagonist substance must effect an inhibition of the smooth muscle contraction induced by the administration of substance P.

It too has been found that the clarified and stabilized culture medium for at least one non-photosynthetic filamentous bacterium satisfies the characteristics defming a substance P antagonist and can thus be used as a substance P antagonist.

Hence, this invention features the use of an effective amount of a culture medium for at least one non-photosynthetic filamentous bacterium, said medium being clarified and stabilized, as a substance P antagonist in cosmetic compositions or for the formulation of pharmaceutical compositions.

The invention also features a cosmetic treatment intended to treat disorders associated with excessive synthesis and/or release of substance P, such that a cosmetic composition as described above is topically applied to the skin, to the scalp and/or to mucous membranes.

The invention also features pharmaceutical compositions intended to treat disorders associated with excessive synthesis and/or release of substance P, such compositions comprising an effective amount of a culture medium for at least one non-photosynthetic filamentous bacterium, as described above.

In addition, this invention also features pharmaceutical compositions intended to treat disorders of the central nervous system, respiratory afflictions, allergic syndromes, inflammation, pain, gastrointestinal disorders, skin disorders, fibrosis, disorders of collagen maturation, cardiovascular disorders, vasospastic disorders, immunological disorders and/or disorders of the urinary tract, comprising an effective amount of a culture medium for at least one non-photosynthetic filamentous bacterium, as described above.

In the field of skin disorders, it is known that certain skin types are more sensitive than others. It is known that many phenomena of skin intolerance exist, the symptoms of which are, in particular, subjective signs which are essentially dysaesthesic sensations. By the term "dysaesthesic sensations" are intended more or less painful sensations experienced in an area of skin, such as stinging, tingling, itching or pruritus, burning, heating, discomfort, tautness, etc.

These phenomena can be the consequence of multiple events, the most common of which will be deemed irritation or inflammation, but certain of which will be due to physiological causes, such as sensitive skin, or even pathological causes such as, for example, allergy.

However, the symptoms of sensitive skin were hitherto poorly characterized and the problem of these skin types was consequently poorly defined. The nature of the process involved in skin sensitivity was not exactly known. Certain researchers considered sensitive skin to be skin which reacted to cosmetic products, while others considered that it was skin which reacted to several external factors, not necessarily associated with cosmetic products. Sensitive skin was also likened to allergic skin.

Tests have been developed to define sensitive skin, for example tests using lactic acid and DMSO which are known to be irritant substances: see, for example, the article by K. Lammintausta et al., *Dermatoses*, 1988, 36, pages 45–49; and the article by T. Agner and J. Serup, *Clinical and Experimental Dermatology*, 1989, 14, pages 214–217.

On account of the ignorance of the characteristics of sensitive skin types, it was hitherto very difficult or even impossible to treat them. They were treated indirectly, for example by limiting, in the cosmetic or dermatological compositions, the use of products having an irritant nature, such as surfactants, preservatives or fragrances, as well as the use of certain cosmetic or dermatological active agents.

After many clinical tests, the assignee hereof has been able to determine the symptoms associated with sensitive skin.

Thus, it has now been found that sensitive skin can be divided into two major clinical forms: irritable and/or reactive skin and intolerant skin.

An irritable and/or reactive skin is a skin which reacts by a pruritus, i.e., by itching or by stinging, to various factors such as the environment, the emotions, foods, the wind, rubbing, shaving, soap, surfactants, hard water having a high calcium concentration, temperature variations or wool. In general, these signs are associated with a dry skin with or without dry patches, or with a skin which displays erythema.

An intolerant skin is a skin which reacts, by sensations of heating, tautness, tingling and/or redness, to various factors such as the environment, the emotions, foods and certain cosmetic products. In general, these signs are associated with a hyperseborrhoeic or acneic skin with or without dry patches, and with erythema.

These phenomena can be generalized over the entire body, but they are usually in well-defined locations such as, for example, the scalp, the face, skin folds, etc.

"Sensitive" scalps have a more unequivocal clinical semeiology: the sensations of pruritus and/or of stinging and/or of inflammation are essentially triggered by local factors such as rubbing, soap, surfactants, hard water having a high calcium concentration, shampoos or lotions. These sensations are also sometimes triggered by factors such as the environment, the emotions and/or foods. Erythema and hyperseborrhoea of the scalp and the presence of dandruff are often associated with the above signs.

Moreover, in certain anatomical regions such as the major folds (groin, genital, axillary, popliteal, anal and submammary regions, and in the fold of the elbows) and the feet, sensitive skin is reflected by pruriginous sensations and/or dysesthesic sensations (heating, stinging) associated in particular with sweat, rubbing, wool, surfactants, certain cosmetic preparations, hard water having a high calcium concentration and/or temperature variations.

This set of intolerance phenomena is always associated with a standard inflammatory process, and more particularly with an inflammatory reaction of neurogenic type since it involves skin nerve fibers.

It has also thus been shown that sensitive skin is not allergic skin. Indeed, allergic skin is skin which reacts to an external agent, an allergen, which triggers an allergic reaction. This is an immunological process which takes place only when an allergen is present and which affects only sensitized individuals. On the other hand, the final result of an allergic reaction is also reflected in an acute inflammatory reaction generally associated with an oedema.

To the contrary, the essential characteristic of sensitive skin, according to the assignee hereof, is a mechanism of response to external factors, which may be the case for any individual, even though individuals said to have sensitive skin react faster thereto than other individuals. This is a nonspecific mechanism and not an immunological one.

Irrespective of the phenomenon envisaged, all of these mechanisms have a common point which is reflected by an inflammatory reaction whose end facet is measured by the release, by the mastocyte cells in the skin, of at least one inflammation mediator such as histamine, serotonin, heparin, leukotrienes, prostaglandins, cytokins, nitrogen monoxide or reactive oxygen-containing species.

The assignee hereof has also developed a test in order to determine whether or not a skin is sensitive. After having carried out many tests with the goal of defining sensitive skin, it has thus been found, surprisingly, that there is a connection between individuals with sensitive skin and those who react to a topical application of capsaicin.

The capsaicin test entails applying, to about 4 cm² of skin, 0.05 ml of a cream comprising 0.075% capsaicin and in noting the appearance of subjective signs induced by this application, such as stinging, burning and itching. In individuals with sensitive skin, these signs appear between 3 and 20 minutes after the application and are followed by the appearance of an erythema which begins at the edge of the zone of application.

Hitherto, capsaicin was used as a medicinal active agent, in particular for treating zona pains. Capsaicin induces a release of neuropeptides, and in particular tachykinins, which originate from epidermal and dermal nerve endings. It has been observed that the physiopathological pattern common to all the conditions of sensitive skin was associated with a great ability to release tachykinins, and more particularly substance P, into the skin. The dysesthesic manifestations which are induced by their release are referred to as being "neurogenic".

Hitherto, a connection between substance P and sensitive skin had not been established. The clinical signs of sensitive skin are essentially subjective: stinging, tingling, pruritus, tautness and heating, and they are occasionally associated with erythemas. These signs are due to nonspecific external factors. The symptoms appear to be essentially localized on the face, the neck and the scalp, but may also appear on the entire body.

Thus, it has now been discovered that one of the essential characteristics of sensitive skin is associated with the release of substance P and therefore that the use of substance P antagonists may make it possible to elicit a preventive and/or curative effect for sensitive skin.

It has thus been envisaged to use substance P antagonists in order to treat sensitive skin. Too, it has now been observed, surprisingly, that the incorporation of a substance P antagonist into a composition intended for topical use makes it possible to avoid the skin irritation and/or dysesthesic sensations and/or pruritus.

The invention thus more particularly features a cosmetic treatment intended to treat sensitive skin, such that a cosmetic composition as described above is topically applied to the skin, to the scalp and/or to mucous membranes.

This invention also features pharmaceutical compositions intended to treat sensitive skin, comprising an effective amount of a culture medium for at least one non-photosynthetic filamentous bacterium, as described above.

The present invention also features the use of an effective amount of a culture medium for at least one non-photosynthetic filamentous bacterium, said medium being clarified and stabilized, in cosmetic compositions or for the formulation of a pharmaceutical compositions, said medium or said compositions being intended to prevent and/or combat skin irritation and/or dry patches and/or erythema and/or heating sensations and/or dysaesthesia and/or pruritus of the skin and/or mucous membranes.

Too, this invention features a cosmetic treatment intended to prevent and/or combat skin irritation and/or dry patches and/or erythema and/or heating sensations and/or dysesthesia and/or pruritus of the skin and/or mucous membranes, such that a cosmetic composition as described above is topically applied to the skin, to the scalp and/or to mucous membranes.

Advantageously according to the invention, an effective amount of a culture medium for at least one non-photosynthetic filamentous bacterium, said medium being clarified and stabilized, can be combined with products normally eliciting an irritant effect which are common in the cosmetic or pharmaceutical field, these products oftentimes being cosmetic or pharmaceutical active agents.

The presence of a substance P antagonist comprising an effective amount of a culture medium for at least one non-photosynthetic filamentous bacterium, said medium being clarified and stabilized, in a cosmetic or pharmaceutical composition which comprises an active species eliciting an irritant response, makes it possible to attenuate this irritant effect considerably, or even to eliminate it altogether.

This also permits increasing the amount of active agent eliciting an irritant response relative to the amount of active agent normally employed, for the purpose of improved efficacy.

Thus, the present invention also features formulating an effective amount of a culture medium for at least one non-photosynthetic filamentous bacterium, such medium being clarified and stabilized, into a cosmetic or pharmaceutical composition also comprising at least one active species eliciting an irritant effect.

This invention also features cosmetic or pharmaceutical compositions comprising, in a cosmetically or pharmaceutically acceptable medium (vehicle, diluent or carrier), an effective amount of a culture medium for at least one non-photosynthetic filamentous bacterium, said medium being clarified and stabilized, and also at least one active species eliciting an irritant effect.

Exemplary compounds eliciting an irritant effect include, for example, surfactants (ionic or nonionic), preservatives, organic solvents or active agents such as α-hydroxy acids (citric acid, malic acid, glycolic acid, tartaric acid, mandelic acid, lactic acid), β-hydroxy acids (salicylic acid and derivatives thereof), α-keto acids, β-keto acids, retinoids (retinol, retinal, retinoic acid), anthralins (dioxyanthranol), anthranoids, peroxides (in particular benzoyl peroxide), minoxidil, lithium salts, antimetabolites, keratolytic agents, vitamin D and derivatives thereof, hair dyes or colorants (para-phenylenediamine and derivatives thereof, aminophenols), fragrancing alcoholic solutions (fragrances, eaux de toilette, aftershave, deodorants), antiperspirants (certain aluminim salts), hair-removing active agents or permanent-waving agents (thiols) and depigmenting active agents (hydroquinone).

The use of a substance P antagonist makes it possible, in particular, to multiply the amount of active agent exhibiting an irritant effect by 2 to 10 times relative to the state of the art, without experiencing any of the discomforts indicated above. Thus, the hydroxy acids can be used at up to 50% of the weight of the composition, or the retinoids at up to 5%, while appreciably reducing the irritant effects thereof.

Thus, it has now been determined that the clarified and stabilized culture medium for at least one non-photosynthetic filamentous bacterium exhibits anti-inflammatory, cicatrizing, antiacne and antiseborrhoeic properties and that it promotes moisturization of the skin.

Hence, the invention features a cosmetic treatment intended to soothe inflammation, to promote cicatrization, to reduce acne and/or seborrhoea and/or to promote moisturization of the skin, whereby a cosmetic composition as described above is topically applied to the skin, to the hair and/or to mucous membranes.

Too, this invention features a pharmaceutical composition intended to soothe inflammation, to promote cicatrization, to reduce acne and/or seborrhoea and/or to promote moisturization of the skin, comprising an effective amount of a culture medium for at least one non-photosynthetic filamentous bacterium, as described above.

The cosmetic treatment, regime or regimen of the invention is advantageously carried out by topically applying the hygienic or cosmetic compositions as described above, according to the usual technique for using these compositions, for example: application of creams, gels, sera, lotions, makeup-removing milks or sunscreen compositions to the skin or to dry hair, application of a hair lotion to wet hair, application of shampoo, or, alternatively, application of toothpaste to the gums.

In order to further illustrate the present invention and the advantages thereof, the following specific examples are given, it being understood that same are intended only as illustrative and in nowise limitative.

In said examples to follow, all parts and percentages are given by weight unless otherwise indicated.

EXAMPLE 1

Preparation of Clarified and Stabilized Culture Medium for at Least one Non-Photosynthetic Filamentous Bacterium A strain of *Vitreoscilla filiformis* (ATCC 15551) was cultured according to the technique described in WO-94/02158. Culturing was carried out at 26° C. for at least 48 hours until a suitable cell concentration corresponding to an optical density at 600 nm of greater than or equal to 1.5 was obtained. The strain was subcultured at 2% V/V in fresh medium every 48 hours until a stable culture was obtained. A 1 liter conical flask containing 200 ml of fresh medium was then inoculated with 4 ml of the above culture.

Culturing in the conical flask was carried out at 26° C. on a culture table agitated at 100 revolutions/minute. The base stock thus obtained served as inoculum for a 10l fermenter. Growth occurred at 26° C., pH 7, 100 revolutions/minute and $pO_2 \geq 15\%$.

After 48 hours of growth, the biomass was transferred into a fermenter with a working capacity of 600 liters, in order to be cultured under the same conditions.

The following Table I culture medium was employed:

TABLE I

| COMPOSITION | CONCENTRATION |
| --- | --- |
| Autolytic extract of Biokar yeast (Ref. 112002) | 2.0 g/l |
| Soybean papain peptone (from PPS-USP Biokar Ref. 1 1601) | 2.0 g/l |
| Heller microelements | 2.0 ml/l |
| Anhydrous glucose | 2.0 g/l |
| $CaCl_2.10H_2O$ | 0.066 g/l |
| Distilled water | 100.0 ml |

The pH was adjusted to 7.15 by addition of 1N sodium hydroxide or potassium hydroxide before sterilization at 121° C. for 20 min.

The composition of the Heller microelements, per 1 l of distilled water, was as shown in Table II:

TABLE II

| | |
| --- | --- |
| $ZnSO_4.7H_2O$ | 1 g |
| $MnSO_4.H_2O$ | 0.076 g |
| $CuSO_4.5H_2O$ | 0.003 g |
| KI | 0.010 g |
| $H_3BO_3$ | 1 g |
| $AlCl_3.6H_2O$ | 0.050 g |
| $NiCl_2.6H_2O$ | 0.030 g |

0.2 g/l of a polymethylsiloxane-type antifoaming agent (Silbione 97350 RP) was added to this culture medium. The temperature was adjusted to between 26° and 30° C., the optimum being 29° C.

A complete growth cycle required about 48 h.

Aeration was regulated by a mass flow meter in order to provide a minimum of 20% dissolved oxygen.

There was virtually no residual glucose at the end of the growth.

The biomass was separated by centrifugation.

This was carried out in an industrial-type centrifuge cooled to 4° C., making it possible to obtain a separating power equivalent to 8000×g, run for 2 minutes.

The culture medium thus harvested could then be stored by freezing for use at a later date.

Before use, the medium was sterilized at a temperature of between 114° C. and 121° C. for 15 to 40 minutes.

EXAMPLE 2

The Capacity of the Medium of Example 1 to Stimulate the Immune Defenses is Studied in this Example (A) Study of the Stimulation of Mouse Splenocytes This study was performed according to the procedure described by L. E. Averill and N. S. Wolf, *Journal of Immunology*, 134, 3859–3863 (1985).

Preparation of Mouse Splenocytes

Balb/C mouse spleens were dilacerated in RPMI 1640 medium (Sigma).

The cell suspension was filtered through a filter of the "cell stainer" type marketed by Nunc in order to remove the cell aggregates. The suspension was then centrifuged at 1000 rpm for 10 minutes at 4° C. The cell pellet was suspended in complete RPMI medium containing 2 mM L-glutamine, 100 units/ml of penicillin, 100 µg/ml of streptomycin, $5 \times 10^{-5}$ M2-mercaptoethanol and 10% foetal calf serum. The cell suspension was adjusted to $2.5 \times 10^6$ cells per ml.

Cell Proliferation Test

Cells as prepared above were distributed in 96-well culture plates (Falcon) at a rate of $2.5 \times 10^5$ cells per well, in a final volume of 100 µl. 20 µl of clarified and stabilized culture medium for at least one non-photosynthetic filamentous bacterium, of Example 1, were added to the final concentrations to be studied. The volume of each well was adjusted to 200 µl by addition of 80 µl of complete RPMI medium. The cells were cultured for 48 and 72 hours. 18 hours before the end of culturing, 1 µCi of tritiated thymidine with a specific activity equal to 82 Ci/mmol (Amersham) was added to each well. At the end of the culturing period, the cells are recovered on a filter. After drying the filter, it was introduced into a liquid scintillation beta-counter in order to determine the radioactivity incorporated into the DNA.

For comparison of the effects, the same test was carried out on cell walls of *Vitreoscilla filiformis*. These cell walls were prepared from the biomass obtained after culturing and separation of the medium, by treatment at 121° C. for 15 minutes. These cell walls were known to have an immunostimulatory effect (WO 94/02158).

Measurement of the radioactivity incorporated into the DNA made it possible to determine the rate of growth of the splenocytes.

The results are reported in the following Table III:

TABLE III

|   | [...]<br>(%) | 48 Hours | | 72 Hours | |
|---|---|---|---|---|---|
|   |   | Average | Standard deviation | Average | Standard deviation |
| CONTROL | 0 | 100 | 0 | 100 | 0 |
| A | 25 | 3218 | 383 | 3554 | 657 |
|   | 12.5 | 4660 | 915 | 4134 | 764 |
|   | 6.25 | 4258 | 929 | 3859 | 1047 |
|   | 3.13 | 3395 | 788 | 4043 | 949 |
|   | 1.56 | 2284 | 589 | 3285 | 782 |
|   | 0.78 | 1760 | 327 | 2430 | 456 |
|   | 0.39 | 1051 | 206 | 2016 | 481 |
|   | 0.19 | 637 | 45 | 1505 | 234 |
| B | 25 | 42 | 25 | 75 | 47 |
|   | 12.5 | 600 | 202 | 589 | 275 |
|   | 6.25 | 1118 | 202 | 949 | 256 |
|   | 3.13 | 1147 | 157 | 1164 | 421 |
|   | 1.56 | 780 | 89 | 1011 | 128 |
|   | 0.78 | 672 | 29 | 831 | 36 |
|   | 0.39 | 509 | 1 | 706 | 99 |
|   | 0.19 | 375 | 16 | 485 | 32 |

A: Culture medium of Example 1;
B: Cell Walls of *Vitreoscilla filiformis*;
CONTROL: Culture medium containing no bacteria;
[...] (%): Concentration of A or B used in the test and expressed as a % (volume/volume for A and weight/volume for B).

The results are expressed as a stimulation index calculated according to the formula: test value/control value ×100.

Values greater than 20 were considered as being positive.

The medium of Example 1 induced growth of mouse splenocytes. The maximum proliferation was obtained at 48 hours of culturing for the 12.5% concentration. The results were superior to those obtained with the *Vitreoscilla filiformis* cell walls.

(B) Study of the Production of Immunoglobulins

Cells as prepared in Example 2 were distributed in 6-well culture plates (Falcon) at a rate of $10 \times 10^6$ cells per well (volume of 2 ml per well).

300 µl of the various test products were added to the test concentrations, which assumed that they were concentrated 10-fold. The volume of each well was adjusted to 3 ml by addition of 0.7 ml of complete RPMI 1640 medium. The cells were cultured for 3 days and the culture supernatants were then removed. The immunoglobulins were assayed using the "Mab-based mouse Ig isotyping kit" (Pharmingen) according to the manufacturer's procedure.

Immunoglobulins are proteins present in the blood which combine with antigens in order for the latter to be recognized and identified as foreign substances by macrophages.

Immunoglobulins are subdivided into different types and sub-types depending on the structure of the constant part of their heavy chain. 5 classes (Ig M, G, A, D and E) are distinguished in mice. Immunoglobulin G is the most abundant immunoglobulin in body fluids, especially extravascular fluids, in which it combats microorganisms and toxins. The G immunoglobulins can be classified into 4 sub-classes (1, 2, 3 and 4).

Immunoglobulin A is the main immunoglobulin in seromucous secretions, in which it defends the outer surfaces of the body.

Immunoglobulin M is a very effective agglutinating agent produced very early in the immune response. It constitutes the first line of defense against bacteriemia.

Only Ig G1, G2a, G2b, G3, M and A were assayed in this test.

For comparison of the effects, the same test was carried out on *Vitreoscilla filiformis* cell walls. These cell walls were prepared from the biomass obtained after culturing and separation of the medium, followed by heat-treatment at 121° C. for 15 minutes.

A positive control was prepared with lipopolysaccharides (LPS) from *Escherichia coli*, which are known to be good immunostimulators.

The results are reported in the following Table IV:

TABLE IV

|   | [...]<br>(%) | IgG1 | IgG2a | IgG2b | IgG3 | IgM | IgA |
|---|---|---|---|---|---|---|---|
| A | 25 | 160 | 159 | 185 | 168 | 129 |   |
|   | 12.5 | 173 | 162 | 188 | 173 | 135 | 175 |
|   | 6.25 | 165 | 152 | 182 | 167 | 131 | 169 |
| B | 12.5 | 142 | 140 | 158 | 135 | 107 | 138 |
|   | 6.25 | 178 | 176 | 203 | 171 | 135 | 174 |
|   | 3.13 | 162 | 162 | 172 | 162 | 131 | 164 |
| C | 0.1 | 168 | 164 | 189 | 189 | 162 | 179 |
|   | 1 | 176 | 176 | 207 | 197 | 168 | 186 |

A: Medium of Example 1;
B: *Vitreoscilla filiformis* cell walls;
C: LPS from *Escherichia coli* (marketed by Sigma) as positive control, used at 10 µg/ml;

[...](%): Concentrations used in the test and expressed as a % (volume/volume for A and weight/volume for B and C).

The results are expressed as a production index calculated according to the formula: Test value/control value ×100

Values above 150 are considered as being positive.

The clarified and stabilized medium induced the production of immunoglobulins by the B cells.

The clarified and stabilized medium increased the growth of splenocytes and the production of immunoglobulins. No toxicity was observed with this medium up to a dose of 25%.

These results clearly demonstrated the immunomodulatory role of the medium according to the invention.

EXAMPLE 3

The following are specific examples of formulations according to the invention. These compositions were formulated by simple admixing of the various components.

| Composition 1 | |
|---|---|
| Dermal composition in cream form: | |
| Medium of Example 1 | 2.0 g |
| Liquid petroleum jelly | 15.0 g |
| Sunflower oil | 5.0 g |
| Stearic acid | 2.0 g |
| Cetyl alcohol | 3.0 g |
| Polyethylene glycol stearate containing 100 EO | 5.0 g |
| Propylene glycol | 3.0 g |
| Preservatives | 0.3 g |
| Purified water qs | 100.0 g |

This cream was applied at a rate of 3 applications per day to burns or wounds in order to accelerate cicatrization.

| Composition 2 | |
|---|---|
| After-sun milk: | |
| Medium of Example 1 | 1.0 g |
| Self-emulsifiable glyceryl monostearate | 3.0 g |
| Liquid petroleum jelly | 4.0 g |
| Wheatgerm oil | 2.0 g |
| Volatile silicone oil | 5.0 g |
| Karite butter | 3.0 g |
| Carbomer 940* | 0.2 g |
| Triethanolamine | 0.2 g |
| Xanthan gum | 0.1 g |
| Glycerol | 3.0 g |
| Fragrancing composition | 0.1 g |
| Preservatives | 0.3 g |
| Purified water qs | 100.0 g |

*Carbomer 940 = commercial trademark denoting a crosslinked polyacrylic acid. This milk was applied to the entire body after exposure to the sun.

| Composition 3 | |
|---|---|
| Sunscreen composition: | |
| Medium of Example 1 | 5.0 g |
| Stearic acid | 3.0 g |
| Cetyl alcohol | 1.5 g |
| Self-emulsifiable glyceryl monostearate | 3.0 g |
| Sunflower oil | 8.0 g |
| Polyacrylamide | 3.0 g |
| Octyl methoxycinnamate | 4.0 g |
| Triethanolamine salt of terephthalylidene-dicamphorsulphonic acid (Mexoryl SX) | 2.6 g |
| Glycerol | 5.0 g |
| Tocopherol | 2.0 g |
| Preservatives | 0.3 g |

| -continued | |
|---|---|
| Composition 3 | |
| Pentasodium ethylenediaminetetramethylene-phosphonate | 0.1 g |
| Purified water qs | 100.0 g |

This emulsion was used to protect the skin against ultraviolet rays and to maintain and stimulate the immune system against sunlight.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for reducing and/or delaying aging of the skin, comprising topically applying to the skin, scalp and/or mucous membranes of an individual in need of such treatment, an effective amount of the cosmetic/phannaceutical composition which comprises an effective active principle amount of a clarified and stabilized culture medium used to culture at least one non-photosynthetic filamentous bacterium, formulated into a cosmetically/pharmaceutically acceptable vehicle, diluent or carrier therefor.

2. A method for stimulating the immune system, comprising topically applying to the skin, scalp and/or mucous membranes of an individual in need of such treatment, an effective amount of the cosmetic/pharmaceutical composition which comprises an effective active principle amount of a clarified and stabilized culture medium used to culture at least one non-photosynthetic filamentous bacterium, formulated into a cosmetically/pharmaceutically acceptable vehicle, diluent or carrier therefor.

3. The method of claim 1, wherein said non-photosynthetic filamentous bacterium belongs to the order Beggiatoales.

4. The method of claim 2, wherein said non-photosynthetic filamentous bacterium belongs to the order Beggiatoales.

5. The method of claim 1 wherein said non-photosynthetic filamentous bacterium belongs to a genus selected from the group consisting of Beggiatoa, Vitreoscilla, Flexithrix and Leucothrix.

6. The method of claim 2 wherein said non-photosynthetic filamentous bacterium belongs to a genus selected from the group consisting of Beggiatoa, Vitreoscilla, Flexithrix and Leucothrix.

7. The method of claim 1 wherein said non-photosynthetic filamentous bacterium is a strain of *Vitreoscilla filiformis*.

8. The method of claim 2 wherein said non-photosynthetic filamentous bacterium is a strain of *Vitreoscilla filiformis*.

9. The method of claim 1 wherein said stabilized and clarified culture medium comprises from 0.0001% to 30% by weight of the administered cosmetic/pharmaceutical composition.

10. The method of claim 2 wherein said stabilized and clarified culture medium comprises from 0.0001% to 30% by weight of the administered cosmetic/pharmaceutical composition.

11. The method of claim 1 wherein said culture medium comprises an acetate carbon source.

12. The method of claim 2 wherein said culture medium comprises an acetate carbon source.

13. The method as defined by claim 1 wherein said culture medium comprises a saccharide carbon source.

14. The method as defined by claim 2 wherein said culture medium comprises a saccharide carbon source.

15. The method of claim 1 wherein said bacterium containing culture medium has been cultured at a temperature ranging from 18° to 40° C.

16. The method of claim 2 wherein said bacterium containing culture medium has been cultured at a temperature ranging from 18° to 40° C.

* * * * *